United States Patent
Zhong

(10) Patent No.: US 7,858,046 B2
(45) Date of Patent: Dec. 28, 2010

(54) DETACHABLE TEST SENSOR CONTAINER HAVING A SYSTEM FOR REDUCING CODING ERRORS

(75) Inventor: Weiping Zhong, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 580 days.

(21) Appl. No.: 11/899,278

(22) Filed: Sep. 5, 2007

(65) Prior Publication Data

US 2008/0066529 A1 Mar. 20, 2008

Related U.S. Application Data

(60) Provisional application No. 60/844,559, filed on Sep. 14, 2006.

(51) Int. Cl.
| B01L 3/00 | (2006.01) |
| G01N 15/06 | (2006.01) |
| G01N 33/00 | (2006.01) |
| G01N 33/48 | (2006.01) |

(52) U.S. Cl. .................. 422/102; 422/50; 422/68.1; 436/43

(58) Field of Classification Search .................. 221/92; 422/50, 102

See application file for complete search history.

(56) References Cited

U.S. PATENT DOCUMENTS

| 2,931,536 | A | * | 4/1960 | Thomasma et al. | ........... 221/41 |
| 5,575,403 | A | | 11/1996 | Charlton et al. | ................ 221/31 |
| 6,908,008 | B2 | * | 6/2005 | Pugh | ........................... 221/135 |
| 2003/0089730 | A1 | * | 5/2003 | May et al. | .................... 221/232 |
| 2003/0186446 | A1 | * | 10/2003 | Pugh | ........................... 436/46 |
| 2004/0007585 | A1 | * | 1/2004 | Griffith et al. | ............... 221/232 |
| 2007/0202007 | A1 | | 8/2007 | Augstein et al. | ............... 422/56 |
| 2007/0264165 | A1 | * | 11/2007 | Chan et al. | .................. 422/104 |
| 2007/0293790 | A1 | | 12/2007 | Bainczyk et al. | ........... 600/583 |
| 2009/0098018 | A1 | * | 4/2009 | Bainczyk et al. | .......... 422/68.1 |

FOREIGN PATENT DOCUMENTS

| DE | 10 2004 057 503 A1 | 6/2006 |
| EP | 1 225 448 A2 | 7/2002 |
| EP | 1 494 021 A1 | 1/2005 |
| WO | WO 2005/088319 A2 | 9/2005 |

OTHER PUBLICATIONS

Written Opinion corresponding to International Patent Application No. PCT/US2007/019878, European Patent Office, dated Sep. 8, 2008, 9 pages.

International Search Report corresponding to International Patent Application No. PCT/US2007/019878, European Patent Office, dated Sep. 8, 2008, 8 pages.

* cited by examiner

*Primary Examiner*—Brian J Sines
(74) *Attorney, Agent, or Firm*—Nixon Peabody LLP

(57) ABSTRACT

A test sensor container that releasably attaches to a testing device for testing an analyte concentration in a fluid sample. The test sensor container comprises a housing, a connector and an opening formed in the housing. The housing contains a plurality of test sensors. The opening formed in the housing receives a test sensor having the fluid sample to be tested by the testing device. The opening includes at least two contact springs for contacting the test sensor to be tested.

11 Claims, 5 Drawing Sheets

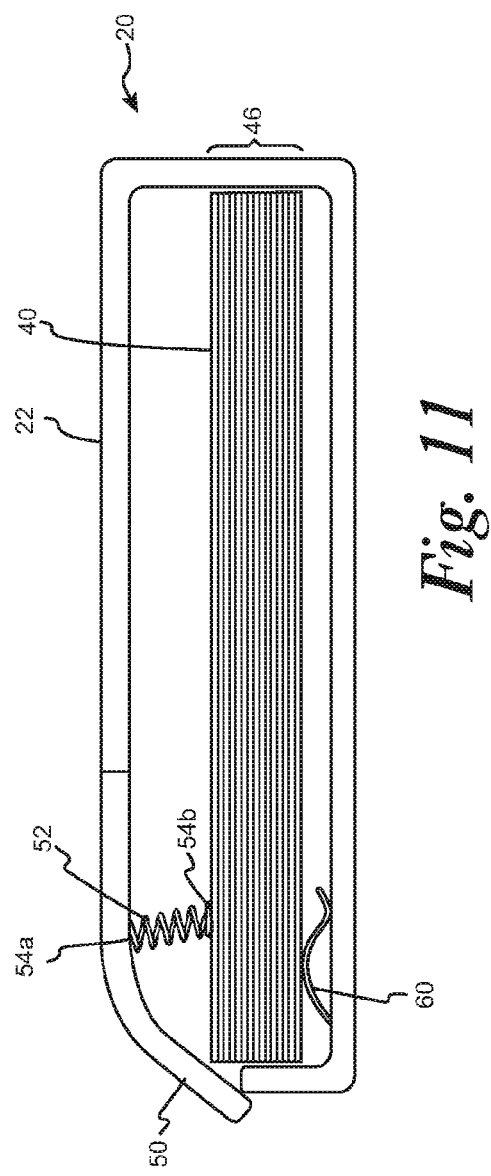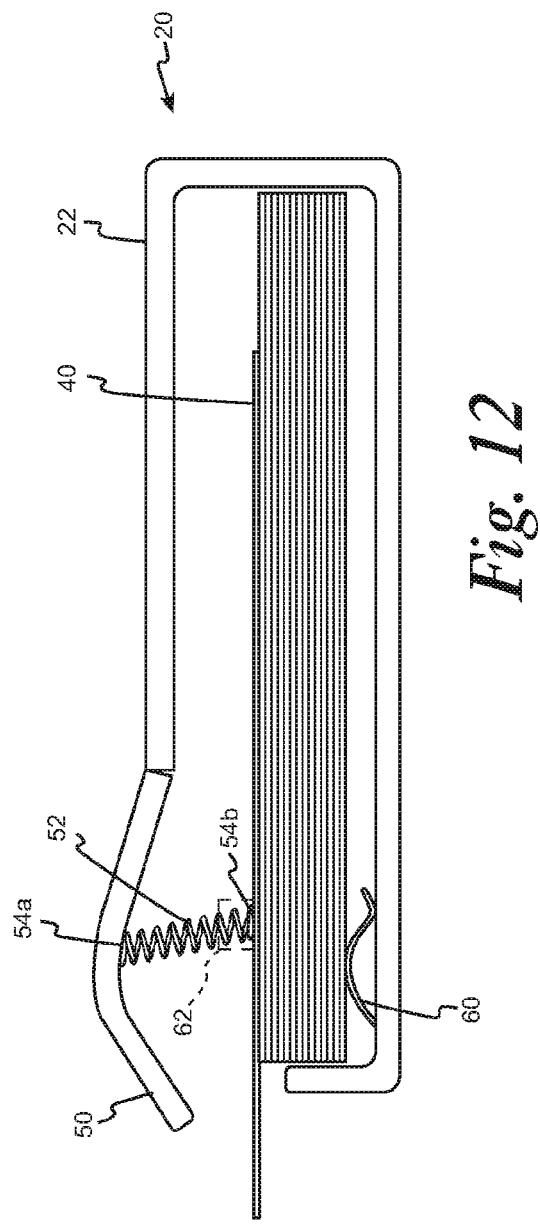

DETACHABLE TEST SENSOR CONTAINER HAVING A SYSTEM FOR REDUCING CODING ERRORS

CROSS-REFERENCE TO RELATED APPLICATION

This application claims priority to U.S. Provisional Application Ser. No. 60/844,559 filed on Sep. 14, 2006, which is incorporated by reference in its entirety.

FIELD OF THE INVENTION

The present invention relates generally to a container for test sensors and, more particularly, to a container for test sensors adapted for use with a testing device to determine an analyte concentration in a liquid sample.

BACKGROUND OF THE INVENTION

Individuals who have irregular blood glucose concentration levels are often medically required to self-monitor their blood glucose concentration level. An irregular blood glucose level can be brought on by a variety of reasons, including illness, such as diabetes. The purpose of monitoring the blood glucose level is to determine the concentration level and then to take corrective action, based on whether the level is too high or too low, to bring the level back within a normal range. The failure to take corrective action may have serious adverse effects on the individual.

Beyond the above-described blood glucose concentration level monitoring, self-testing systems are also used for determining the presence or concentration of other analytes in body fluids, such as, for example, cholesterol, alcohol, and hemoglobin in blood, interstitial fluid, or chemical substances in saliva.

One method of monitoring a person's blood glucose level is with a portable, hand-held, blood glucose testing device. The portable nature of these devices enables users to conveniently test their blood glucose levels wherever the users may be. The test device receives a test sensor for harvesting the blood for analysis. The test sensor, one of which is required for each test, contains a reaction area including a reagent for producing a measurable reaction with the glucose indicative of the blood glucose concentration level. The test sensor harvests the blood for reaction with the reagent stored within.

Prior art test devices exist that contain a plurality of test sensors or test strips in either a circular sensor packaging container or a cartridge sensor packaging container. An exemplary prior art circular sensor packaging container is disclosed in U.S. Pat. No. 5,575,403. One drawback with prior art circular sensor packaging containers is the limited number of test sensors contained in the container. The number of test sensors contained in the sensor packaging container is limited by the physical space available for the sensor packaging container within the handheld test device. Therefore, a need exists for a test sensor container that is not limited by the size of the testing device.

Additionally, there is a need to insure that the test sensors, which are placed in the testing device, are the appropriate test sensors. Otherwise, miscoding of the test sensor can occur, which could result in the user relying on erroneous test results. Therefore, a need exists for a testing system that avoids the miscoding and use of inappropriate test sensors.

SUMMARY OF THE INVENTION

According to one embodiment of the present invention, a test sensor container adapted for use with a testing device for testing an analyte concentration in a fluid sample is provided. The test sensor container comprises a housing adapted to contain a plurality of test sensors. The housing is adapted to releasably connect to the testing device. The plurality of test sensors includes at least two electrodes at the ends of the test sensors. At least one connector is connected to the housing. The at least one connector is adapted to releasably connect the housing to the testing device. An opening is formed in the housing which is adapted to receive a test sensor having the fluid sample to be tested by the testing device. The opening has at least two contact springs adapted to contact the test sensor to be tested.

According to another embodiment of the present invention, a method for determining an analyte concentration in a fluid sample is provided. The method comprises the acts of providing a test sensor container having a housing adapted to contain a plurality of test sensors. The test sensor container releasably connects to a testing device via at least one connector. The method also comprises receiving a test sensor having the fluid sample to be tested through an opening in the test sensor container. The test sensor has at least two electrodes. The opening contains at least two contact springs. The method further comprises contacting the at least two contact springs with the at least two electrodes of the test sensor and measuring the analyte concentration via the testing device.

According to a further embodiment of the present invention, a system for testing an analyte concentration in a fluid sample is provided. The system comprises a test sensor container including a housing for handling a plurality of test sensors and an opening for receiving a test sensor having the fluid sample to be tested. The opening has at least two contact springs. The system further comprises a testing device releasably connected to and in communication with the test sensor container such that when the at least two contact springs of the test sensor container contact the test sensor having the fluid sample, the testing device determines the analyte concentration in the fluid sample.

According to a further embodiment of the present invention, a test sensor container adapted for use with a testing device for testing an analyte concentration in a fluid sample is provided. The test sensor container comprises a housing for handling a plurality of test sensors, the housing includes a lid. The test sensor container also comprises a spring having a first end and a second end. The first end connects to the lid and the second end contacts at least one of the plurality of test sensors in the housing. The second end is adapted to move the at least one of the plurality of test sensors out of the housing, one at a time, when the lid is opened by a user.

According to a further embodiment of the present invention, a test sensor container adapted for use with a testing device for testing an analyte concentration in a fluid sample is provided. The test sensor container comprises a housing for handling a plurality of test sensors. The housing is adapted to releasably connect to the testing device. The test sensor further comprises at least one connector for connecting the housing to the testing device and a counter for counting when at least one of the plurality of test sensors has been removed from the housing, such that the testing device will only operate when the counter reads that at least one of the test sensors has been removed.

The above summary of the present invention is not intended to represent each embodiment or every aspect of the present invention. The detailed description and Figures will describe many of the embodiments of the present invention.

BRIEF DESCRIPTION OF THE DRAWINGS

FIG. 11 is a cross-sectional side view of a test sensor container having a mechanism for removing a test sensor from the test sensor container according to another embodiment of the present invention.

FIG. 12 is a cross-sectional side view of a test sensor container showing a test sensor being removed from the test sensor container according to another embodiment of the present invention.

Figure 1:
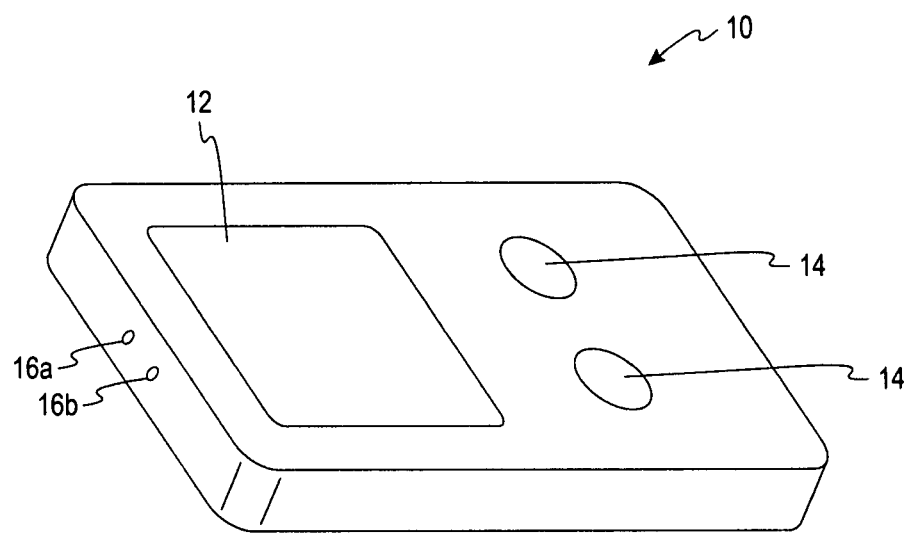
FIG. 1 is a top perspective view of a testing device according to one embodiment of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF THE ILLUSTRATED EMBODIMENTS

Referring now to the drawings, and initially to FIG. 1, a testing device 10 for testing an analyte concentration in a fluid sample is shown according to one embodiment of the present invention. While the following discussion may describe the use of a testing device 10 for determining the glucose concentration in blood, it is understood that the present invention may be employed in determining the concentration of other analytes in other types of samples. Analytes that may be measured using the present invention include glucose, lipid profiles (e.g., cholesterol, triglycerides, LDL and HDL), microalbumin, hemoglobin $A_{1C}$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, or other body fluids like ISF (interstitial fluid) and urine.

The testing device 10 comprises a display 12, at least one user input mechanism 14 and at least one connector 16. The display 12 may include any of several types of displays. For example, the display 12 may include an LCD display, a graphics display, a plasma display, a backlit display, a combination segmented/graphic display or any other suitable display. The user input mechanism 14 is adapted to allow the user to make selections relating to one or more user features and may include, for example, buttons, scroll bars, touch screens, or any combination of such items.

The at least one connector 16 includes a connecting mechanism for releasably connecting a test sensor container (see, e.g., FIG. 2) to the testing device 10. It is desirable that the testing device 10 includes two connectors 16a, 16b. The connectors 16 may be comprised of metal objects, such as stainless steel, copper, or metal-coated materials, that connect to metal objects in a test sensor container as described below. The testing device 10 may also include a memory device (not shown) that is adapted to store analyte concentration readings, etc.

Figure 2:
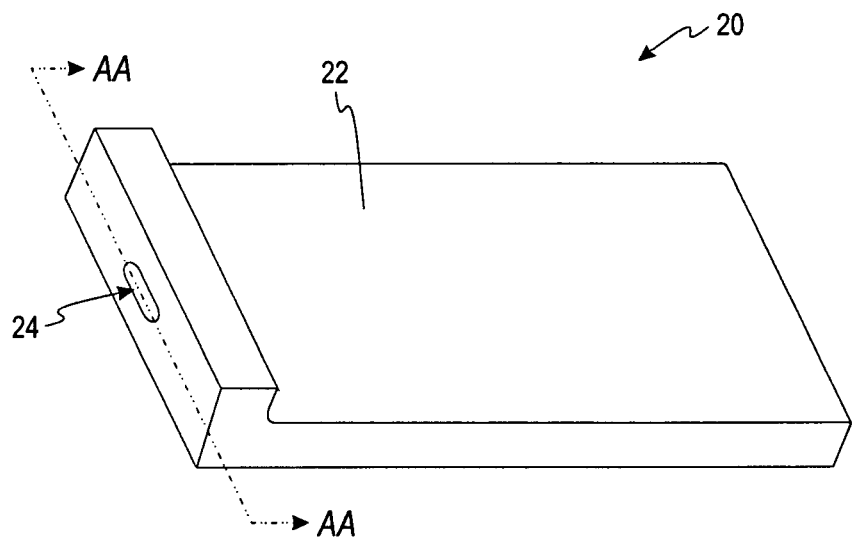
FIG. 2 is a top perspective view of a test sensor container according to one embodiment of the present invention.

FIG. 2 shows a test sensor container 20 comprising a housing 22 adapted to contain a plurality of test sensors (not shown). The housing 22 may contain any number of test sensors, including up to 50 test sensors. The housing 22 may be comprised of a molded polymeric material according to one embodiment of the present invention. Using a molded polymeric material for the housing 22 increases the structural rigidity of the test sensor container 20. The test sensor container 20 may be molded with a desiccant to provide a dry environment for the reagents contained on the test sensors. The desiccant may either be molded with the test sensor container 20 or contained in a small chamber. As shown in FIGS. 11 and 12, the test sensor container 20 may also comprise a lid that allows a user to insert the test sensors to be stored in the test sensor container 20.

Figure 5:
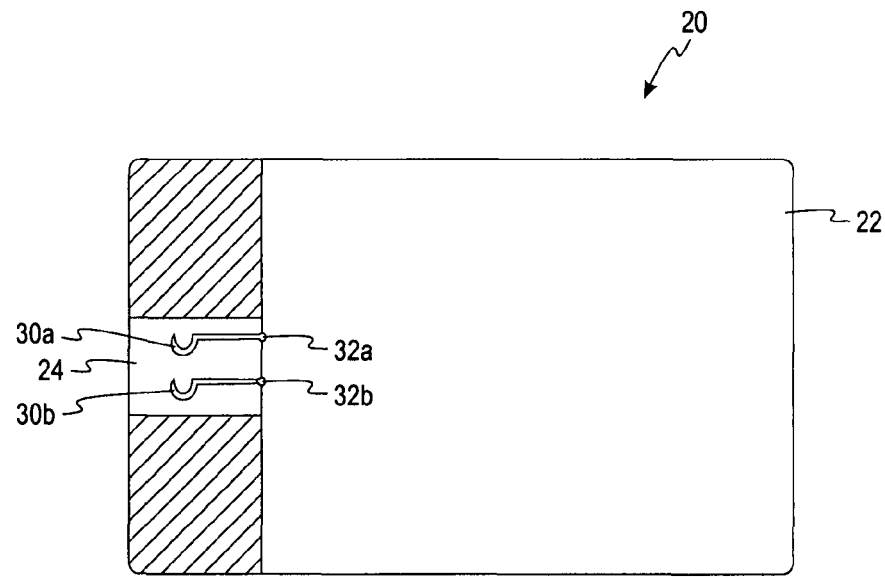
FIG. 5 is a cross-sectional view of the test sensor container of FIG. 2 taken generally through the plane AA-AA showing an opening containing two contact springs according to one embodiment of the present invention.

Referring to FIG. 2, the test sensor container 20 also forms an opening 24. The opening 24 receives a test sensor for testing via the testing device 10. As is shown in FIG. 5, the opening 24 includes at least two contact springs 30a, 30b, which are discussed below in more detail. The opening 24 may range from about 0.5 cm to about 1.0 cm in length to about 0.1 cm to about 0.2 cm in width. Desirably, the opening 24 is about 0.5 cm by about 0.1 cm. The opening 24 in the test sensor container 20 is in communication with the at least one connector 16 of the testing device 10.

Figure 3:
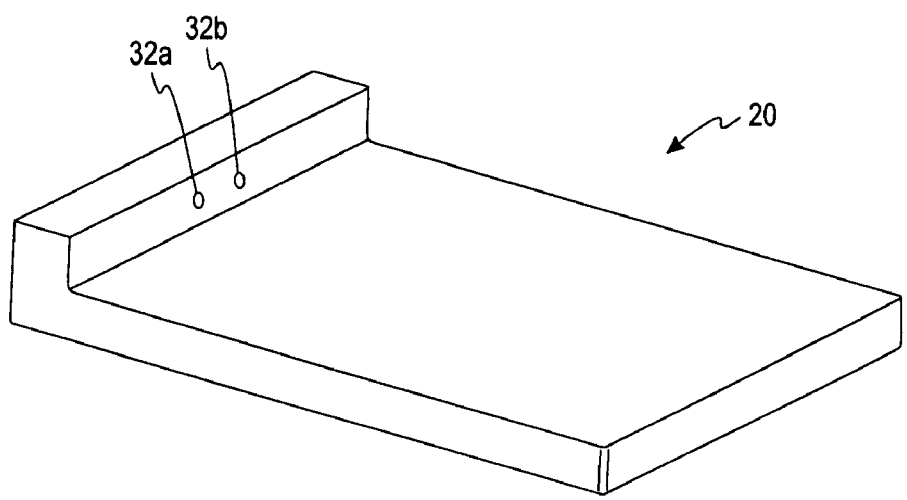
FIG. 3 is a top perspective view of the test sensor container of FIG. 2.

As shown in FIG. 3, the test sensor container 20 also includes at least one connector 32 corresponding to the at least one connector 16 of the testing device 10. The connectors 16, 32 are adapted to releasably connect the test sensor container 20 and the testing device 10. Desirably, the testing device 10 and test sensor container 20 include at least two connectors 16a, 16b and 32a, 32b, respectively. In some embodiments, the two connectors 16a, 16b, 32a, 32b serve as positive and negative electrodes that connect to the test sensor to conduct an electric current. It is contemplated that more than two connectors may also be used in the present invention. This allows for more than one substance to be analyzed, such as, for example, glucose and $H_{AIB}$.

Figure 4:
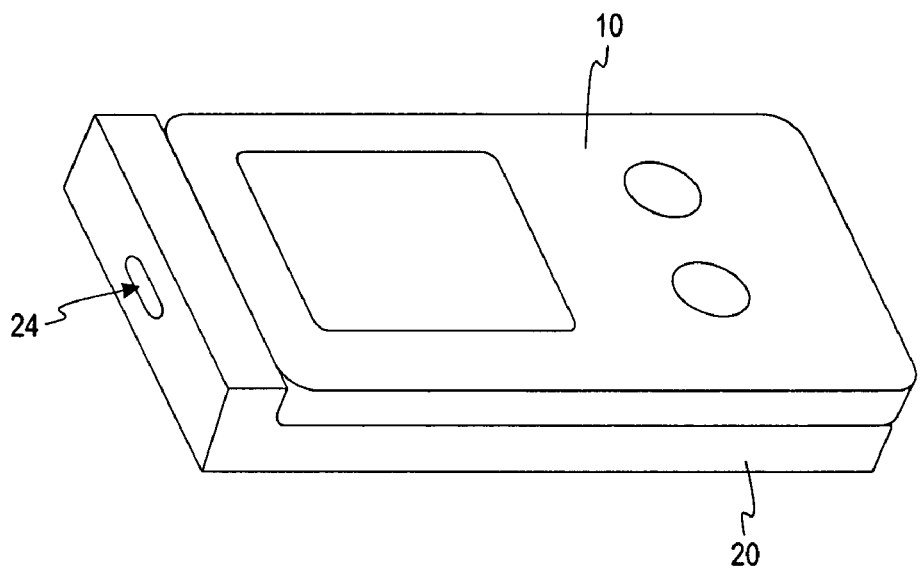
FIG. 4 is a top perspective view of the test sensor container of FIG. 2 connected to the testing device of FIG. 1 according to one embodiment of the present invention.

FIG. 4 shows the test sensor container 20 releasably connected to the testing device 10. The test sensor container 20 and the testing device 10 may be adapted to be mated via a snap fit feature that allows the test sensor container 20 and the testing device 10 to be attached as a single unit. Once connected, a user is able to insert a test sensor 40 (shown in FIG. 7) into the opening 24 and provide a fluid sample for testing. Testing of the fluid sample may take place if the test sensor 40 is an appropriate test sensor to be used with the testing device 10. If the test sensor 40 is not an appropriate test sensor, then the testing device 10 will not operate to test the fluid sample for the desired analyte concentration.

Turning now to FIG. 5, a cross-sectional view of the test sensor container 20 is shown. The housing 22 contains the unused test sensors (not shown). The opening 24 contains the at least two contact springs 30a, 30b that are attached to the connectors 32a, 32b. The two contact springs 30a, 30b and the connectors 32a, 32b operate to conduct electrical signals for testing a fluid sample for an analyte concentration. The two contact springs 30a, 30b may be comprised of materials such as stainless steel, copper or metal-coated materials.

Figure 6:
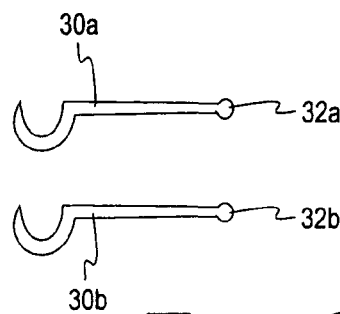
FIG. 6 is an enlarged side view of the two contact springs of FIG. 5 according to one embodiment of the present invention.

The two contact springs 30a, 30b, shown in FIG. 6, may be of different shapes and/or lengths. The two contact springs 30a, 30b may also be located at various positions in the opening 24. The two contact springs 30a, 30b shown in FIG. 5 extend horizontally from the connectors 32a, 32b into the approximate center of the opening 24. The two contact springs 30a, 30b are generally parallel to each other and correspond to positive and negative contacts when used with an appropriate test sensor 40.

Figure 7:
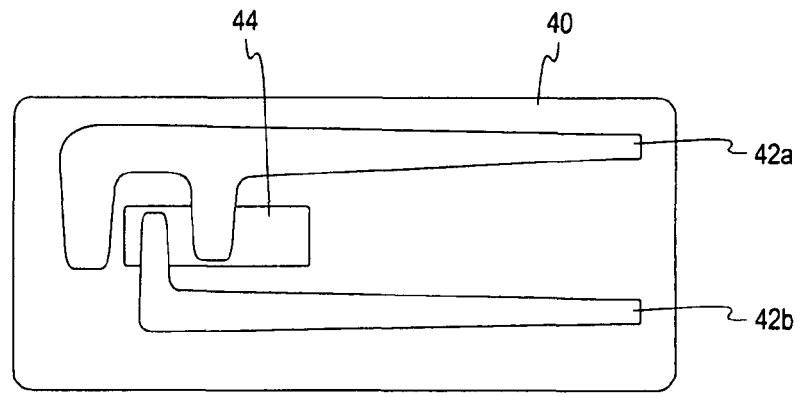
FIG. 7 is an enlarged top view of a test sensor having electrodes on one end of the test sensor according to one embodiment of the present invention.
Figure 8:
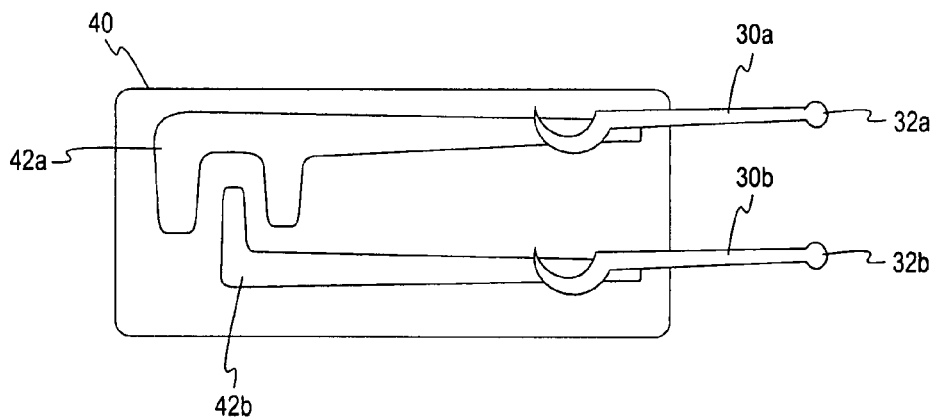
FIG. 8 is an enlarged top view of the test sensor of FIG. 7 contacting the contact springs of FIG. 6 according to one embodiment of the present invention.

The test sensor 40 of FIG. 7 includes two electrodes 42a, 42b at one end of the test sensor 40. As illustrated in FIG. 8, upon insertion of the test sensor 40 into the opening 24 of the test sensor container 20, the electrode 42a will contact the contact spring 30a. Similarly, the electrode 42b will contact the contact spring 30b. If an appropriate contact is made between the contact springs 30a, 30b and the electrodes 42a, 42b, the testing device operates to determine the analyte concentration in a fluid sample 44 contained on the test sensor 40. If an inappropriate contact occurs, such as if only one electrode 42a contacts a contact spring 30a, or if one electrode 42a contacts the wrong contact spring 30b, or if no contact occurs between the electrodes 42a, 42b and the contact springs 30a, 30b, then the testing device 10 will not operate to test an analyte concentration.

Figure 9:
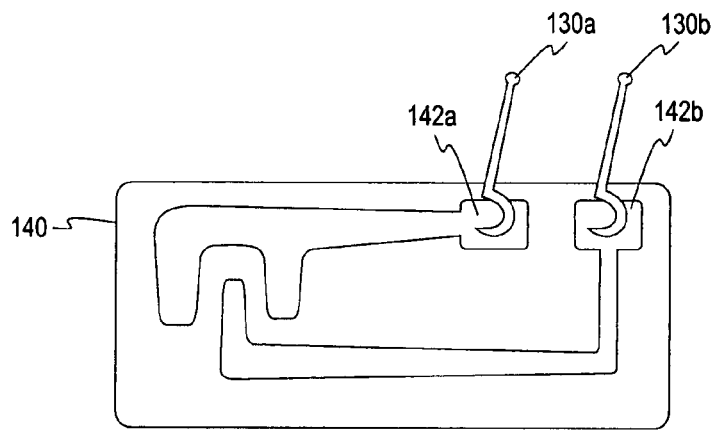
FIG. 9 is an enlarged top view of the test sensor of FIG. 7 contacting the contact springs of FIG. 6 according to yet another embodiment of the present invention.

In another embodiment shown in FIG. 9, the contact springs 130a, 130b are positioned at different locations in the opening 24 such that the contact springs 130a, 130b will only contact the electrodes of test sensors 140 that have a specific orientation. For example, in FIG. 9, contact springs 130a, 130b are positioned such that they will only contact electrodes 142a, 142b that are located in one corner of the test sensor 140. Requiring that the contact springs 130a, 130b and the electrodes 142a, 142b be located in certain positions in the opening 24 and on the test sensor 140, respectively, insures that the testing device 10 will only be able to operate when the correct test sensors 140 are used to test for a particular analyte concentration.

If, for example, a test sensor 40 having electrodes 42a, 42b as shown in FIG. 8 is inserted into an opening 24 having the contact springs 130a, 130b as shown in FIG. 9, the testing device 10 would not be able to operate to determine an analyte concentration as the electrodes 42a, 42b would not contact the contact springs 130a, 130b. Thus, the testing device 10 will not operate due to the requirement of using a specific test sensor 40 with a specific testing system, including the test sensor container 20 and testing device 10 of the present invention.

Other configurations in addition to those described in FIGS. 8 and 9 are contemplated by the present invention. For example, other configurations may consist of having the contact springs 30a, 30b in different locations in the opening 24, such as in upper or lower corners or on opposite sides of the opening 24, or having one contact spring 30a in one corner and the other contact spring 30b in another corner of the opening 24, etc. It is contemplated that various other configurations may be used.

Figure 10:
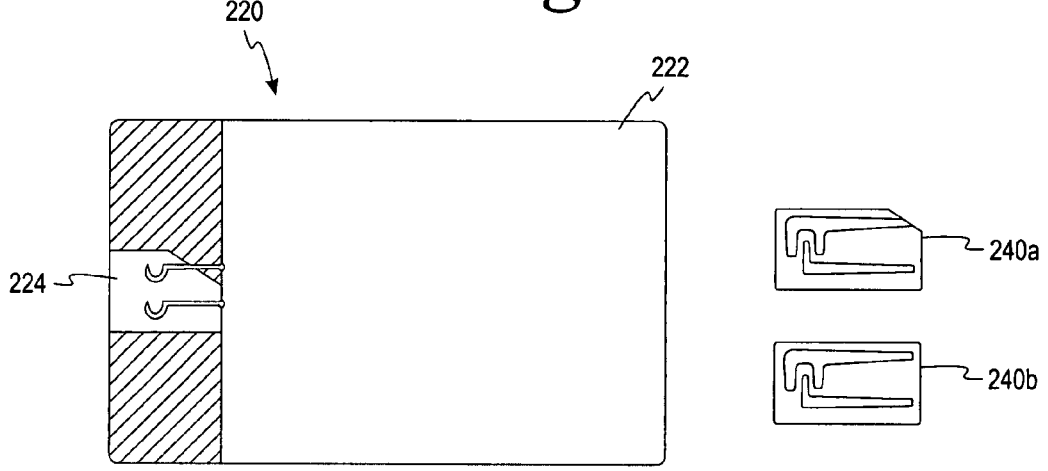
FIG. 10 is a cross-sectional view of the test sensor container of FIG. 2 taken generally through the plane AA-AA showing an opening containing two contact springs according to a further embodiment of the present invention.

It is also contemplated that another way to prevent miscoding is to have an opening in a test sensor container that is specific to the shape of a test sensor 40. For example, in one embodiment shown in FIG. 10, the opening 224 is shaped or configured to accept a test sensor 240a having a matching shape or configuration. If a user tries to insert a test sensor 240b that does not have the matching shape or configuration, then the test sensor 240b will not be accepted into the opening 224 and possible use and/or miscoding of an inappropriate test sensor has been avoided. Only a test sensor 240a having the appropriate shape (i.e., with one specific corner having different dimensions than the other corners) will allow the testing system to operate. Thus, the lack of interchangeability of test sensors prevents miscoding and use of inappropriate test sensors 240. This may be particularly important when different lots of sensors 240 are available and only a certain type of test sensor 240 should be used for a particular type of testing (i.e., testing for glucose rather than testing for fructose).

The test sensor container 20 of the present invention may also be adapted to include different mechanisms for assisting a user in removing the test sensors 40 contained therein. For example, FIG. 11 shows a test sensor container 20 having a lid 50 that may be opened to remove a test sensor 40 from a plurality of test sensors 46. The test sensor container 20 also contains a spring 52. A first end 54a of the spring 52 is connected to the lid 50. A second end 54b of the spring 52 contacts at least one of the plurality of test sensors 40 contained in the housing 22. The second end 54b of the spring 52 is adapted to move at least one of the plurality of test sensors 46 out of the housing 22 when the lid 50 is opened by a user (see FIG. 12).

The second end 54b of the spring 52 may comprise an optional object (schematically illustrated at 62 in FIG. 12), such as a piece of rubber material or a hook, that contacts the test sensor 40 to assist in removing the test sensor 40 from the test sensor container 20. In the embodiment shown in FIG. 12, as the lid 50 opens, the second end 54b of the spring 52, which is in contact with the test sensor 40, is pulled forward toward the lid 50 of the test sensor container 20. This movement brings a portion of the test sensor 40 out of the test sensor container 20 such that a user is able to remove the test sensor 40 in an easier fashion. This is especially useful for older users or users with limited dexterity.

To further increase the ease of removing a test sensor 40 from the test sensor container 20, the test sensor container 20 may comprise a mechanism or device 60 for assisting in moving the plurality of test sensors 46 in a direction toward the lid 50 of the housing 22. The mechanism or device 60 helps to facilitate the removal of the test sensor 40 by moving the plurality of test sensors 46 upward such that they are closer to the lid 50 of the test sensor container 20 and thus are easier to remove.

The test sensor container 20 has dimensions that generally range from about 50 mm to about 100 mm in length, from about 25 mm to about 60 mm in width and from about 5 mm to about 10 mm in depth. The dimensions are desirably about 75 mm in length, about 50 mm in width and about 5 mm in depth.

In a further embodiment of the present invention, the test sensor container 20 is adapted to comprise a counter (not shown) for counting the number of test sensors 40 in the test sensor container 20. When one of the plurality of test sensors 40 has been removed from the housing 22, the counter has a reading of, for example, "−1". In such an embodiment, the testing device 10 only operates when the counter reads "−1." If the counter reads any other number besides "−1," the testing device 10 will not operate. This prevents an inappropriate test sensor 40 from being used, particularly when the test sensor container 20 is empty and a user wishes to test a fluid sample using a replacement test sensor.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the alternative embodiments.

Alternative Embodiments

Alternative Embodiment A

A test sensor container adapted for use with a testing device for testing an analyte concentration in a fluid sample, the test sensor container comprising:

a housing adapted to contain a plurality of test sensors, the housing adapted to releasably connect to the testing device, the plurality of test sensors including at least two electrodes at the ends of the test sensors;

at least one connector connected to the housing, the at least one connector adapted to releasably connect the housing to the testing device; and an opening formed in the housing, the opening adapted to receive a test sensor having the fluid sample to be tested by the testing device, the opening having at least two contact springs adapted to contact the test sensor to be tested.

Alternative Embodiment B

The test sensor container of alternative embodiment A, wherein the at least two contact springs are located at a predetermined distance in the opening of the test sensor container.

Alternative Embodiment C

The test sensor container of alternative embodiment A, wherein the at least two contact springs are located at a predetermined location in the opening of the test sensor container.

Alternative Embodiment D

The test sensor container of alternative embodiment A, wherein the at least two contact springs are arranged to contact the at least two electrodes of the test sensor to be tested.

Alternative Embodiment E

The test sensor container of alternative embodiment D, wherein the at least two contact springs contact the at least two electrodes based on a predetermined pattern or design.

Alternative Embodiment F

The test sensor container of alternative embodiment A, wherein the opening is adapted to receive a test sensor having a specific shape.

Alternative Embodiment G

A method for determining an analyte concentration in a fluid sample, the method comprising the acts of:

providing a test sensor container having a housing adapted to contain a plurality of test sensors, the test sensor container releasably connected to a testing device via at least one connector;

receiving a test sensor having the fluid sample to be tested through an opening in the test sensor container, the test sensor having at least two electrodes, the opening containing at least two contact springs;

contacting the at least two contact springs with the at least two electrodes of the test sensor; and measuring the analyte concentration via the testing device.

Alternative Embodiment H

The method of alternative embodiment G, wherein the at least two contact springs and the at least two electrodes are positioned at predetermined distances to allow the contact to occur.

Alternative Embodiment I

The method of alternative embodiment G, wherein the at least two contact springs and the at least two electrodes are positioned at predetermined locations to allow the contact to occur.

Alternative Embodiment J

The method of alternative embodiment G, wherein the at least two contact springs contact the at least two electrodes based on a predetermined pattern or design.

Alternative Embodiment K

The method of alternative embodiment G, wherein the opening is adapted to receive a test sensor having a specific shape.

Alternative Embodiment L

A system for testing an analyte concentration in a fluid sample, the system comprising:

a test sensor container including a housing for handling a plurality of test sensors and an opening for receiving a test sensor having the fluid sample to be tested, the opening having at least two contact springs; and a testing device releasably connected to and in communication with the test sensor container such that when the at least two contact springs of the test sensor container contact the test sensor having the fluid sample, the testing device determines the analyte concentration in the fluid sample.

Alternative Embodiment M

A test sensor container adapted for use with a testing device for testing an analyte concentration in a fluid sample, the test sensor container comprising:

a housing for handling a plurality of test sensors, the housing including a lid;

a spring having a first end and a second end, the first end connected to the lid, the second end contacting at least one of the plurality of test sensors in the housing, the second end adapted to move the at least one of the plurality of test sensors out of the housing, one at a time, when the lid is opened by a user.

Alternative Embodiment N

The test sensor container of alternative embodiment M, further comprising a mechanism for assisting in moving the at least one of the plurality of test sensors in a direction toward the lid of the housing to facilitate the removal of the at least one test sensor.

Alternative Embodiment O

The test sensor container of alternative embodiment M, wherein the second end of the spring includes a rubber object for contacting the at least one of the plurality of test sensors.

Alternative Embodiment P

The test sensor container of alternative embodiment M, wherein the second end of the spring includes a hook for contacting the at least one of the plurality of test sensors.

Alternative Embodiment Q

A test sensor container adapted for use with a testing device for testing an analyte concentration in a fluid sample, the test sensor container comprising:
a housing for handling a plurality of test sensors, the housing adapted to releasably connect to the testing device;
at least one connector for connecting the housing to the testing device; and
a counter for counting when at least one of the plurality of test sensors has been removed from the housing, such that the testing device will only operate when the counter reads that at least one of the test sensors has been removed.

What is claimed is:

1. A test sensor container adapted for use with a testing device for testing an analyte concentration in a fluid sample, the test sensor container comprising:
a housing for handling a plurality of test sensors, the housing including a lid;
a spring having a first end and a second end, the first end connected to the lid, the second end contacting at least one of the plurality of test sensors in the housing, the second end adapted to move the at least one of the plurality of test sensors out of the housing, one at a time, when the lid is opened by a user.

2. The test sensor container of claim 1, further comprising a mechanism for assisting in moving the at least one of the plurality of test sensors in a direction toward the lid of the housing to facilitate the removal of the at least one test sensor.

3. The test sensor container of claim 1, wherein the second end of the spring includes a rubber object for contacting the at least one of the plurality of test sensors.

4. The test sensor container of claim 1, wherein the second end of the spring includes a hook for contacting the at least one of the plurality of test sensors.

5. The test sensor container of claim 1, further comprising at least one connector connected to the housing, the at least one connector adapted to releasably connect the housing to the testing device.

6. The test sensor container of claim 1, wherein the housing defines an opening configured to receive a test sensor having the fluid sample to be tested by the testing device, the opening having at least two contact springs adapted to electrically couple the test sensor with the testing device.

7. The test sensor container of claim 6, wherein the at least two contact springs are located at a predetermined distance in the opening of the test sensor container.

8. The test sensor container of claim 6, wherein each of the test sensors includes at least two electrodes, the at least two contact springs being arranged to contact the at least two electrodes of the test sensor when the test sensor is received in the opening of the housing.

9. The test sensor container of claim 8, wherein the at least two contact springs contact the at least two electrodes based on a predetermined pattern or design.

10. The test sensor container of claim 6, wherein the opening is adapted to receive a test sensor having a specific shape.

11. The test sensor container of claim 1, further comprising a counter for counting when at least one of the plurality of test sensors has been removed from the housing, wherein the testing device operates only when the counter reads that at least one of the test sensors has been removed.

* * * * *